US010118119B2

(12) United States Patent
Sappok et al.

(10) Patent No.: US 10,118,119 B2
(45) Date of Patent: Nov. 6, 2018

(54) RADIO FREQUENCY PROCESS SENSING, CONTROL, AND DIAGNOSTICS NETWORK AND SYSTEM

(71) Applicant: CTS Corporation, Lisle, IL (US)

(72) Inventors: Alexander G. Sappok, Cambridge, MA (US); Paul A. Ragaller, Dorchester, MA (US); Leslie Bromberg, Sharon, MA (US); Andrew D. Herman, Granger, IN (US)

(73) Assignee: CTS Corporation, Lisle, IL (US)

( * ) Notice: Subject to any disclaimer, the term of this patent is extended or adjusted under 35 U.S.C. 154(b) by 0 days.

(21) Appl. No.: 15/461,128

(22) Filed: Mar. 16, 2017

(65) Prior Publication Data

US 2017/0182447 A1    Jun. 29, 2017

Related U.S. Application Data

(63) Continuation-in-part of application No. 14/733,525, filed on Jun. 8, 2015, and a continuation-in-part of application No. 14/733,486, filed on Jun. 8, 2015.
(Continued)

(51) Int. Cl.
*F01N 9/00*    (2006.01)
*F01N 3/035*   (2006.01)
(Continued)

(52) U.S. Cl.
CPC ......... *B01D 46/0086* (2013.01); *F01N 3/021* (2013.01); *F01N 11/00* (2013.01);
(Continued)

(58) Field of Classification Search
CPC ......... Y02T 10/47; Y02T 10/20; Y02T 10/24; Y02T 10/26; F01N 9/002; F01N 2560/12;
(Continued)

(56) References Cited

U.S. PATENT DOCUMENTS 4,024,452 A    5/1977  Seidel
4,042,879 A    8/1977  Ho et al.
(Continued)

FOREIGN PATENT DOCUMENTS

CN    1032238 A    4/1989
CN    101078692 A    11/2007
(Continued)

OTHER PUBLICATIONS

Rights et al: "Tille Preparation and characterisation of ceria particles," 2013; Retrieved from the Internet: URL:htts:// :: ora.ucc.ie/bitstream/handle/10468/1141 /MorrisVNA_ PhD2013 .pdf.

*Primary Examiner* — Alesa Allgood
(74) *Attorney, Agent, or Firm* — Daniel Deneufbourg

(57) ABSTRACT

A radio frequency sensing, control, and particulate matter diagnostics network and system and method and, more specifically, a radio frequency particulate filter diagnostics system comprising a housing including an inlet connected to a source of particulate matter, a particulate filter in the housing and adapted for filtering the particulate matter, and a radio frequency sensor adapted to detect conditions of abnormal particulate filter or system operation and including at least one radio frequency probe configured to be in contact with the housing for the particulate filter housing and adapted to receive radio frequency signals and a radio frequency control unit in communication with the radio frequency probe.

10 Claims, 4 Drawing Sheets

Related U.S. Application Data

(60) Provisional application No. 62/311,020, filed on Mar. 21, 2016.

(51) Int. Cl.

| | | |
|---|---|---|
| *F01N 3/00* | (2006.01) | |
| *F01N 3/10* | (2006.01) | |
| *B01D 46/00* | (2006.01) | |
| *F01N 11/00* | (2006.01) | |
| *G01N 22/00* | (2006.01) | |
| *F01N 3/021* | (2006.01) | |

(52) U.S. Cl.
CPC ........... *F01N 11/005* (2013.01); *G01N 22/00* (2013.01); *B01D 2279/30* (2013.01); *F01N 9/002* (2013.01); *F01N 2550/04* (2013.01); *F01N 2550/24* (2013.01); *F01N 2560/12* (2013.01); *F01N 2900/0416* (2013.01); *F01N 2900/0418* (2013.01); *F01N 2900/08* (2013.01); *F01N 2900/1602* (2013.01); *F01N 2900/1606* (2013.01)

(58) Field of Classification Search
CPC ............. F01N 2550/04; F01N 2560/05; F01N 2900/1606; F01N 13/009; F01N 2370/22; F01N 11/00; F01N 3/021; F01N 3/0253; F01N 3/103; F01N 2560/14; F01N 11/002; F01N 11/005; F01N 2550/00; G01N 22/00; G01N 15/0618; G01N 25/72

See application file for complete search history.

(56) References Cited

U.S. PATENT DOCUMENTS

| | | | |
|---|---|---|---|
| 4,477,771 A | 10/1984 | Nagy et al. | |
| 4,689,553 A | 8/1987 | Haddox | |
| 5,074,112 A | 12/1991 | Walton | |
| 5,103,181 A | 4/1992 | Gaisford et al. | |
| 5,142,595 A | 8/1992 | Chester | |
| 5,157,340 A | 10/1992 | Walton et al. | |
| 5,369,369 A | 11/1994 | Cutmore | |
| 5,423,180 A | 6/1995 | Nobue et al. | |
| 5,447,635 A | 9/1995 | Viscardi et al. | |
| 5,497,099 A | 3/1996 | Walton | |
| 5,500,599 A | 3/1996 | Stange | |
| 5,557,933 A | 9/1996 | Numata et al. | |
| 6,131,386 A | 10/2000 | Trumble | |
| 6,147,503 A | 11/2000 | Nelson et al. | |
| 6,507,308 B1 | 1/2003 | Ono et al. | |
| 6,630,833 B2 | 10/2003 | Scott | |
| 6,819,849 B1 | 11/2004 | Tangonan et al. | |
| 6,854,261 B2 | 2/2005 | Williamson et al. | |
| 7,157,919 B1 | 1/2007 | Walton | |
| 7,357,822 B2 | 4/2008 | Hamahata et al. | |
| 7,679,374 B2 | 3/2010 | Bromberg et al. | |
| 8,384,396 B2 | 2/2013 | Bromberg et al. | |
| 8,384,397 B2 | 2/2013 | Bromberg et al. | |
| 8,889,221 B2 | 11/2014 | Sappok | |
| 9,144,831 B2 | 9/2015 | Sappok et al. | |
| 9,399,185 B2 | 7/2016 | Bromberg et al. | |
| 9,400,297 B2 | 7/2016 | Bromberg et al. | |
| 2001/0003898 A1 | 6/2001 | Miller et al. | |
| 2001/0007571 A1 | 7/2001 | Murphy et al. | |
| 2002/0005725 A1 | 1/2002 | Scott | |
| 2004/0200198 A1 | 10/2004 | Inoue et al. | |
| 2005/0011278 A1 | 1/2005 | Brown et al. | |
| 2005/0213548 A1 | 9/2005 | Benson et al. | |
| 2005/0241295 A1* | 11/2005 | Breuer | B01D 53/944 60/274 |
| 2006/0027511 A1 | 2/2006 | Brown et al. | |
| 2006/0070373 A1 | 4/2006 | Huang et al. | |
| 2006/0101793 A1 | 5/2006 | Gregoire et al. | |
| 2006/0138082 A1 | 6/2006 | Strang | |
| 2006/0229466 A1 | 10/2006 | Arhancet et al. | |
| 2007/0000218 A1 | 1/2007 | Wirth et al. | |
| 2007/0022746 A1 | 2/2007 | Decou et al. | |
| 2007/0024289 A1 | 2/2007 | Knitt et al. | |
| 2007/0056274 A1 | 3/2007 | Wills | |
| 2007/0068157 A1 | 3/2007 | Kurtz | |
| 2007/0072567 A1* | 3/2007 | Nagai | H01Q 3/26 455/205 |
| 2007/0101705 A1 | 5/2007 | Knitt | |
| 2007/0125075 A1 | 6/2007 | Zanini-Fisher et al. | |
| 2007/0125349 A1 | 6/2007 | Zanini-Fisher et al. | |
| 2007/0130923 A1 | 6/2007 | Dye et al. | |
| 2007/0169469 A1 | 7/2007 | Knitt | |
| 2007/0209333 A1 | 9/2007 | Kondou | |
| 2007/0214862 A1 | 9/2007 | Kubinski et al. | |
| 2008/0018442 A1 | 1/2008 | Knitt | |
| 2008/0059093 A1 | 3/2008 | Bromberg et al. | |
| 2008/0066621 A1 | 3/2008 | Naito et al. | |
| 2008/0092499 A1 | 4/2008 | Otsuka et al. | |
| 2008/0110143 A1 | 5/2008 | Chen et al. | |
| 2008/0264036 A1 | 10/2008 | Bellovary | |
| 2009/0038294 A1 | 2/2009 | Anderson et al. | |
| 2009/0295509 A1 | 12/2009 | Master et al. | |
| 2010/0101409 A1 | 4/2010 | Bromberg et al. | |
| 2010/0102828 A1 | 4/2010 | Bromberg et al. | |
| 2012/0138093 A1 | 6/2012 | Sappok et al. | |
| 2013/0125745 A1 | 5/2013 | Bromberg et al. | |
| 2013/0127478 A1* | 5/2013 | Bromberg | B01D 46/0086 324/639 |
| 2013/0298530 A1* | 11/2013 | Carlill | F01N 3/0235 60/274 |
| 2014/0116028 A1 | 5/2014 | Sappok et al. | |
| 2015/0123688 A1 | 5/2015 | Sappok et al. | |
| 2015/0132187 A1* | 5/2015 | Takaoka | F01N 3/2066 422/111 |
| 2015/0355110 A1 | 12/2015 | Sappok et al. | |
| 2015/0358091 A1 | 12/2015 | Sappok et al. | |
| 2016/0061128 A1* | 3/2016 | Nicholson | F02D 41/0245 60/274 |
| 2016/0109425 A1 | 4/2016 | Sappok et al. | |
| 2017/0211453 A1 | 7/2017 | Sappok et al. | |

FOREIGN PATENT DOCUMENTS

| | | |
|---|---|---|
| DE | 3317215 A1 | 11/1983 |
| DE | 102004016725 A1 | 2/2006 |
| EP | 0097416 A1 | 1/1984 |
| EP | 0356040 A2 | 2/1990 |
| JP | 4-505665 A | 10/1992 |
| WO | 92/02807 A1 | 2/1992 |
| WO | 93/05388 A1 | 3/1993 |
| WO | 00/50743 A1 | 8/2000 |
| WO | 2004/074670 A2 | 9/2004 |
| WO | 2005/060653 A2 | 7/2005 |
| WO | 2005/093233 A1 | 10/2005 |
| WO | 2006/002037 A2 | 1/2006 |
| WO | 2007/130896 A2 | 11/2007 |
| WO | 2009031600 A2 | 3/2009 |
| WO | 2010/074812 A1 | 7/2010 |
| WO | 2011/156477 A2 | 12/2011 |
| WO | 2014064406 A1 | 5/2014 |
| WO | 2015/188188 A1 | 12/2015 |
| WO | 2015/188189 A1 | 12/2015 |
| WO | 2017/165220 A1 | 9/2017 |

\* cited by examiner

RADIO FREQUENCY PROCESS SENSING, CONTROL, AND DIAGNOSTICS NETWORK AND SYSTEM

CROSS-REFERENCE TO RELATED APPLICATIONS

This patent application claims priority and benefit of the filing date of and is a continuation-in-part of U.S. patent application Ser. No. 14/733,525 filed on Jun. 8, 2015 and U.S. patent application Ser. No. 14/733,486 filed on Jun. 8, 2015, the disclosure and contents of which are expressly incorporated herein in their entireties by reference.

This patent application also claims priority and benefit of the filing date of U.S. Provisional Patent Application Ser. No. 62/311,020 filed on Mar. 21, 2016, the disclosure and contents of which is expressly incorporated herein in its entirety by reference.

GOVERNMENT SPONSORSHIP

This invention was made with government support under Award No. IIP 1330313 awarded by the National Science Foundation. The government has certain rights in the invention.

FIELD OF THE INVENTION

This invention relates generally to a radio frequency process sensing, control, and diagnostics network and system and method and, more specifically, to a radio frequency particulate filter diagnostics network and system and method.

BACKGROUND OF THE INVENTION

This invention is directed to a radio frequency process sensing, control, and diagnostics network and system and, more specifically, a radio frequency particulate filter diagnostics network and system of the type disclosed in United States Patent Application Publication US 2015/0358091 A1 and US 2015/0355110 A1 published on Dec. 10, 2015, the disclosure and contents of which are incorporated herein in their entireties by reference as though fully set forth herein, and which has been adapted for sensing, control, and diagnosing conditions of abnormal filter or system operation.

By way of background, particulate filter failures are most often caused by malfunctions or failures of other engine or vehicle components upstream of the particulate filter. Examples of such upstream malfunctions and failures include but are not limited to injector failures, turbocharger failures, coolant leaks, oil leaks, use of incorrect fuels or lubricants, poor engine maintenance, missing or dirty air filters, restricted intake air flow, and the like.

The aforementioned upstream malfunctions may result in excessive soot or particulate matter (PM) loading of the particulate filter, or water, fuel, oil, or coolant collecting on the filter, in one example. Oftentimes, early-warning signs of these upstream failure modes may not be detected until the problem has become exacerbated to the point where the exhaust particulate filter itself also fails, or its performance Is severely degraded. Therefore, there is a need to detect signs of potential upstream system malfunctions or failures before the particulate filter is irreversibly impacted.

Damage to the particulate filter, which could result in particulate matter escaping or passing through the filter, includes cracking of the channel walls, loss of one or more channel end-plugs, or melting of the filter material. Removal of all or part of the particulate filter from the exhaust system, such as with a straight-pipe or bypass system, also may result in excess PM emissions. Therefore, there is a need to detect conditions which may result in excessive PM levels passing through the particulate filter.

Pressure sensor and model-based approaches for detecting conditions of abnormal filter or system operation suffer from the following deficiencies: pressure measurements lack the resolution to detect failure conditions resulting in PM escaping from the filter at the mandated on-board diagnostic (OBD) limits. This deficiency has been well-documented in the technical literature, and is the reason why the system is not currently used for OBD; the approach provides only an indirect method of estimating the PM loading level on the filter; differential pressure sensors directly measure the pressure drop across the filter (not the PM loading level), which is confounded by a large number of parameters such as exhaust flow rate, temperature, ash loading levels, soot distribution, filter design, etc.; the system only functions over a limited range of operating conditions and does not serve as a continuous monitor; pressure-drop measurements are unreliable at low exhaust flow conditions (idle or engine off), during regeneration, during frequent transient operations, and following filter aging once ash has accumulated in the filter; and models (virtual sensors) rely on a known set of operating conditions to accurately estimate filter loading levels; and the systems by definition, do not function well during error conditions or abnormal operation, such as filter malfunctions or failures, as these conditions are outside the capabilities of the models.

Soot sensors suffer from the following deficiencies: soot sensors monitor the soot concentration in a portion of the exhaust gas downstream of the filter and, as a result, the sensors are incapable of monitoring any engine or system malfunctions upstream of the filter and thus incapable of providing advance warning of potential failure conditions; soot sensors do not directly monitor the state of the filter and more specifically only monitor soot in the exhaust downstream of the filter, i.e., the sensor can only provide an indication of a filter failure after the filter has already failed and soot emissions have exceeded the threshold limits; soot sensor accuracy is also affected by exhaust flow velocity, location of the sensing element in the exhaust pipe (as it only samples a small volume of the flow which may not be representative of the total flow), temperature, particle morphology and composition, and accumulation of deposits (ash, catalyst/washcoat particles) as the sensor ages; accumulation type soot sensors do not provide a continuous monitor but rather cycle from a measuring state to a regeneration state and the regeneration state generally requires additional energy input to burn off any accumulated soot on the sensing element; accumulation type soot sensors do not directly monitor the soot particle number or mass in the exhaust stream, but rather the time for sufficient soot to accumulate on the sensing element, thereby providing only an indirect indication of soot levels in the exhaust; soot sensors suffers from poor durability, the accumulation of contaminants (such as ash), as well as thermal shock (water in the exhaust), which limits the sensor life as well as the sensor accuracy over its useful life; and in order to further improve measurement accuracy, many OBD approaches utilizing soot sensors still require predictive models to estimate engine-out soot levels for comparison with the downstream soot sensor measurements.

The RF sensor network and system and methods of sensing, control, and diagnostics of the present invention advantageously provide the dual function and benefit of improving the control and operation of the particulate filter as well as diagnosing the state of the filter for OBD applications and detecting engine system malfunctions.

Still more specifically, the RF sensor network and system and methods of sensing, control, and diagnostics of the present invention resolve and overcome the problems and deficiencies of the current approaches and methods as discussed above and provide at least the following benefits: unlike the currently employed indirect approaches, the RF sensor of the present invention provides a direct measurement of the particulate filter loading state; RF sensing enables early detection of signs of upstream engine or system failures or malfunctions before the particulate filter is irreversibly damaged; RF sensing can be used to monitor soot leaking or escaping from the particulate filter; RF sensing samples the entire filter, and therefore the entire volume of exhaust passing through it; RF sensing can continually monitor the overall operating conditions of the particulate filter including engine off conditions; the RF sensing element, an electrically-conducting rod antenna, is a passive element that, unlike accumulation type soot sensors, does not require active cleaning or regeneration; the RF sensing element provides increased durability relative to soot sensors as the sensing element is not subject to the same failure modes due to fouling, water or condensation exposure, temperature effects, and the like; and the RF sensing approach, unlike pressure sensors or soot sensors, is completely unaffected by exhaust flow rate.

SUMMARY OF THE INVENTION

The present invention is directed to a radio frequency sensing, control, and particulate matter diagnostics system comprising a housing including an inlet connected to a source of particulate matter, a particulate filter in the housing adapted for filtering the particulate matter, a radio frequency sensor adapted to detect conditions of abnormal particulate filter or system operation, the radio frequency sensor including at least one radio frequency probe in contact with the housing for the particulate filter and adapted to receive radio frequency signals; and a radio frequency control unit in communication with the radio frequency probe.

In one embodiment, the radio frequency sensor is adapted to monitor the time rate of change of the response of the radio frequency sensor to detect a rate of particulate matter accumulation in the particulate filter above or below a threshold value.

In one embodiment, the source of particulate matter is an engine and the particulate matter accumulation is soot, ash, water, coolant, oil, or fuel.

In one embodiment, the radio frequency sensor monitors the time rate of change in the magnitude, frequency or phase of the radio frequency signals.

In one embodiment, the radio frequency sensor detects the absence of the particulate filter or a portion of the filter.

In one embodiment, the absence of the particulate filter or a portion thereof in the housing is detected by sensing a change in the magnitude, frequency, or phase of the radio frequency signals outside a threshold range of the magnitude, frequency, or phase of the radio frequency signals with the particulate filter present in the system.

In one embodiment, the radio frequency sensor is adapted to detect a rate of accumulation of particulate matter below a threshold rate via a comparison of the rate of particulate matter accumulated in the particulate filter over a defined period of time with a known rate of particulate matter accumulation during normal filter operation.

In one embodiment, the radio frequency sensor is adapted to monitor changes in the temperature response of the system.

In one embodiment, the source of particulate matter is an engine and the radio frequency sensor is adapted to monitor engine shutdown events and the radio frequency control unit stores a historical record of changes in the temperature response of the system based on selected measured or derived parameters, the measured or derived parameters including calculated particulate matter load at the time of engine shutdown, exhaust temperature at the time of engine shutdown, periodic or continuous radio frequency measurement values during cool down of the engine, time for the system to reach a threshold temperature, and detection of an unintended rise in temperature after engine shutdown.

In one embodiment, the radio frequency sensor is adapted to monitor the response of the system to an external stimulus.

In one embodiment, the external stimulus is a momentary, controlled increase or decrease in particulate matter emissions.

In one embodiment, the radio frequency sensor is adapted to monitor changes in an expected particulate matter signature in response to the external stimulus and the expected particulate matter signature is derived from existing radio frequency sensor measurement data.

In one embodiment, the radio frequency sensor is adapted to sense the response of the system to selected system inputs in order to relate the input and output radio frequency signals via a transfer function.

In one embodiment, the source of particulate matter is an engine, the particulate matter is soot, and the radio frequency sensor is adapted to monitor a particulate filter regeneration event for oxidizing the accumulated soot in the particulate filter.

The present invention is also directed to a radio frequency diagnostics system comprising a cavity including an inlet connected to a source of contaminant material, an internal element in the cavity configured to capture or store the contaminant material, a radio frequency sensor adapted to conduct a radio frequency measurement and monitor the state of the cavity, the radio frequency sensor including at least one radio frequency probe in contact with the cavity and adapted to detect conditions of abnormal operation of the cavity, the internal element, or the source of contaminant material, and a control unit configured to determine a preferable condition for the radio frequency measurement.

In one embodiment, the radio frequency sensor utilizes one or more resonant modes to determine spatial location of the abnormal operation.

In one embodiment, the preferable condition for conducting a radio frequency measurement is determined to be a condition with negligible soot oxidation.

In one embodiment, the preferable condition for conducting a radio frequency measurement is an intrusive test.

Other advantages and features of the present invention will be more readily apparent from the following detailed description of the preferred embodiments of the invention, the accompanying drawings, and the appended claims.

BRIEF DESCRIPTION OF THE DRAWINGS

These and other features of the invention can best be understood by the description of the accompanying FIGS. as follows.

DETAILED DESCRIPTION

The present invention is directed to a radio frequency process sensing, control, and diagnostics network and system and, more specifically, to a radio frequency particulate filter system of the type disclosed in United States Patent Application Publication US 2015/0358091 A1 and US 2015/0355110 A1 published on Dec. 10, 2015, the disclosure and contents of which are incorporated herein by reference in their entirety as though fully set forth herein, and which has been adapted for detecting, sensing, controlling, and diagnosing conditions of abnormal filter or system operation as described in more detail below.

Specifically, and as disclosed in United States Patent Application Publication US 2015/0358091 A1 and US 2015/0355110 A1 published on Dec. 10, 2015, the system may be comprised of a particulate filter housed in a conductive enclosure forming a resonant cavity or waveguide; one or more antennas or radio frequency transmitting or receiving probes or sensors configured to be in electrical contact with the filter housing; and at least one inlet configured to direct a flow into the filter housing and connected to an engine or source of particulate matter or contaminant material.

Figure 1:
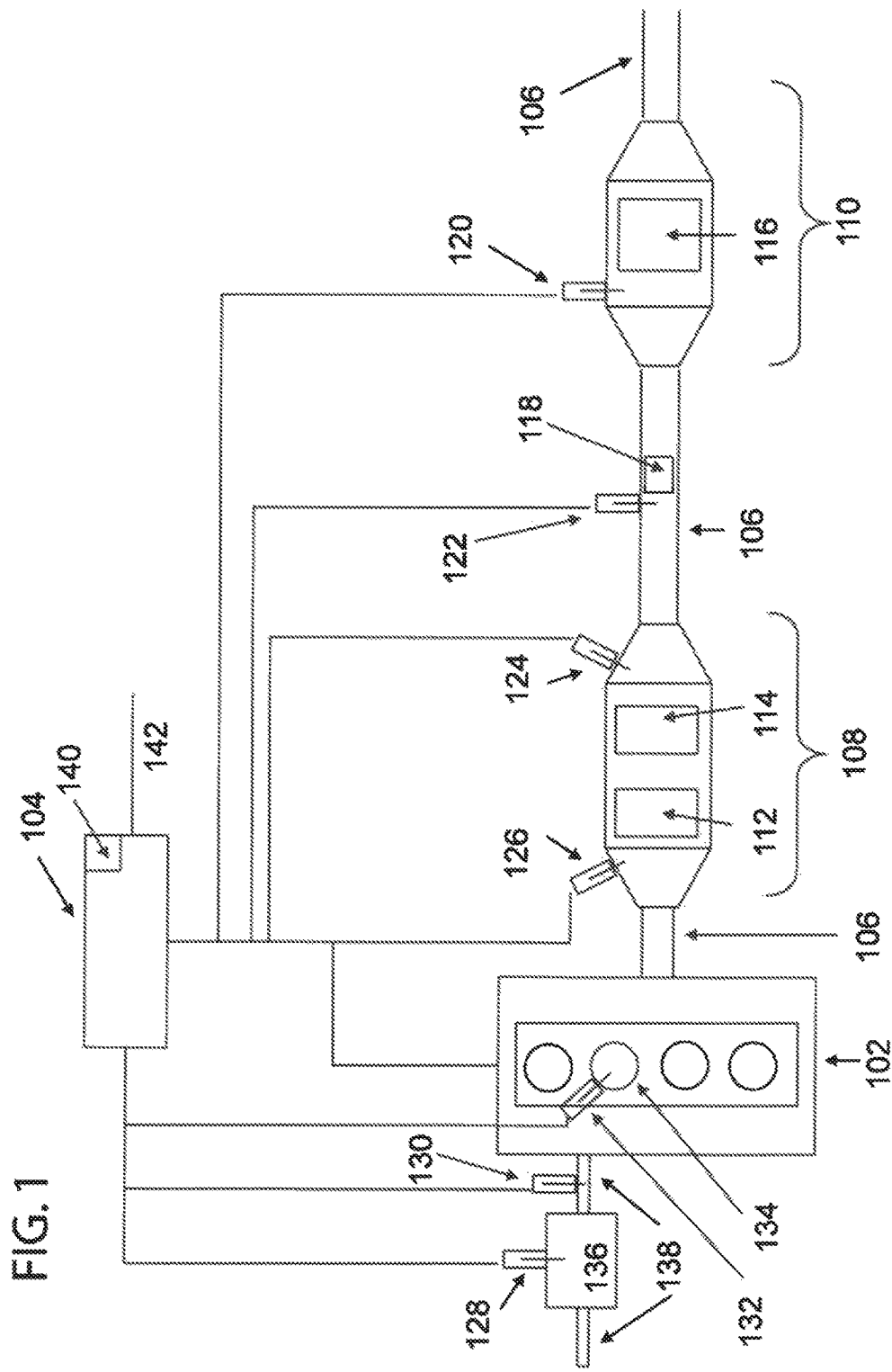
FIG. 1 is a schematic diagram of a plant or process system such as, for example, a vehicle engine and exhaust system monitored and controlled by a radio frequency network and system in accordance with the present invention.

FIG. 1 depicts a plant such as an engine and exhaust system monitored by a radio frequency system. The plant may be any type of plant, such as a chemical plant, food processing plant, power plant, refinery, distillery, or any type of plant or process. The plant or reactor may be a flowing reactor, or it could be a batch reactor.

A machine 102, such as a vehicle engine in the example shown in FIG. 1 or a plant in another example, has an outlet connection, such as a conduit or inlet 106, connected to various components and sensors. Machine 102 generates an output stream, such as an exhaust stream of contaminant or particulate material or matter, or any other stream, that is directed through conduit 106. In the embodiment shown, conduit 106 is connected to first and second modules 108 and 110 which, in the embodiment shown, comprise resonant cavities, and which in another embodiment may comprise waveguides.

In the embodiment shown, module 108 is a particulate filter housing or cavity, such as a housing or cavity for a gasoline or diesel particulate filter or internal element configured to capture or store the incoming contaminant or particulate material or matter. Module 108 contains a catalyst element 112, which may be a three-way catalyst (TWC), an oxidation catalyst (OC), a selective catalytic reduction catalyst (SCR), a lean NOx trap (LNT), or any other type of catalyst, and a filter element 114 such as a particulate filter.

In the embodiment shown, module 110 is a catalyst housing or cavity containing a catalyst internal element 116 such as an SCR, LNT, TWC, ammonia storage, hydrocarbon trap, or any other type of catalyst. In another embodiment, the modules 108 and 110 may be omitted and in another embodiment, more than two modules may be present. Each module may contain one or more internal elements, such as catalysts, filters or membranes in one example, or no internal elements in another example.

Conduit 106 also contains one or more internal elements 118 such as a filter, catalyst, mixer, diffuser, or other element. Radio frequency (RF) probes 120, 122, 124, and 126 including, for example, rod antennas, loop antennas, waveguides, dielectric resonators, or any other suitable RF signal transmission and receiving probes are adapted to monitor the state of the cavities 108 and 100 and to detect the abnormal operation or failure of the cavities 108 and 110, the internal cavity elements, or source of contaminant material as described in more detail below and are located and mounted at various positions along conduit 106 or on or in modules 108 and 110.

Additional conduits 138, including for example intake ducts, fuel lines, oil lines, coolant lines are connected to machine 102. Conduit 138 supplies an inlet stream to plant or machine 102. Conduit 138 contains one or more modules 136 such as an air filter housing, oil filter housing, fuel filter housing, radiator, EGR cooler, fuel tank, oil tank, urea tank or any other type of module, cavity, or wave guide. In the embodiment shown, radio frequency probes 120 or 130 are located and mounted in conduit 138 and module 136.

In the embodiment shown, the radio frequency probe 132 is installed in an engine cylinder 134. Additional probes, not pictured, may also be installed in other components of machine 102. Radio frequency probes or sensors 120, 122, 124, 126, 128, 130, and 132 are connected to a control unit 104 that is configured to determine a preferable condition for conducting a radio frequency measurement. A single or multiple control units 104 may be used to monitor and control all radio frequency probes.

Although not show, it is understood that additional sensors, such as temperature sensors, pressure sensors, gas composition sensors (NOx, PM, Oxygen, Ammonia) or any other types of sensors may be used and connected to control unit 104 or to another control unit (not shown) which may be in communication with control unit 104.

Control unit 104 is connected to machine 102 and may be connected to another control unit, such as an engine control unit or process control unit (not shown). Control unit 104 contains a processing unit and computer readable storage medium 140 containing instructions, algorithms, data, lookup tables, and any other information necessary to control the connected sensors and machine. Control unit 104 contains a connection 142 which may be a communication connection, such as Ethernet, USB, analog, CAN, serial, or some other type of connection or power connection. Connection 142 may be connected to the plant control unit, to the engine control unit (ECU) in a vehicle, or to signal to the operator of the status of the unit and of potential problems.

Control unit 104 also contains hardware or electronics used to transmit radio frequency signals, such as an oscillator or synthesizer, as well as a detector for detecting radio frequency signals such as a diode or power detector or any other type of detector. Control unit 104 may further contain mixers, splitters, directional couplers, switches, amplifiers and other components for controlling, modulating, transmitting, and monitoring radio frequency signals.

Control unit 104 is configured to transmit and receive radio frequency signals through any of the radio frequency probes 120, 122, 124, 126, 128, 130, or 132. Each probe may be independently controlled to transmit, receive, or transmit and receive radio frequency signals, such as in a multi-port network including transmission, reflection, and transmission or reflection. For example, probe 122 may transmit a radio frequency signal which may be detected by one or more probes 126, 124, 122, or 120. In another example, probe 126 may transmit a radio frequency signal that may be received only by probe 126 or by probe 124. Any number of probes may be used and one probe may or may not communicate with another probe.

The radio frequency signals may span a frequency range such as to establish one or more resonant modes, or may span a frequency range that does not include a resonant mode, or may be at a single frequency. The various modules 108, 110, 136, and conduit 106 or 138, or machine components 134 may serve as microwave resonant cavities or waveguides, or may contain resonators (such as dielectric resonators) that can be used to sample a limited region of the device being monitored. The radio frequency signal, including resonance curve, absolute amplitude, relative amplitude (i.e., normalized to the power being transmitted by the probe), phase, resonant frequency shift, frequency shift, or some derivative thereof including local or absolute maxima or minima, frequency shift, phase shift, average value, quality factor, summation, area, peak width, or other parameter may be correlated to the state of the system and used to monitor changes in the loading state of the system.

Changes in the dielectric properties within the cavities or waveguides may be used to monitor or detect one or more of the following parameters: amount of material, type of material, spatial distribution of the material, physical or chemical properties of the material, environmental conditions such as temperature, pressure, humidity, or other related factors, position or level including the position of a piston within a cylinder, crank angle, linear or rotational position, or the volume of a liquid in a tank, reservoir, or conduit such as a fuel tank, oil sump, urea tank, or any other tank or reservoir or pipe or hose, cavity or waveguide integrity, the rate of change of a process parameter, and the health or state of the material within the cavity or waveguide.

Control unit 104 transmits and receives signals from one or more of the radio frequency probes to monitor the state of various system components and functions. In the embodiment shown, machine 102 is an engine such as an internal combustion engine and the module 136 is an air filter, an oil filter, a fuel filter, a radiator, and EGR cooler, an intercooler, tank or reservoir, or similar device and probe 128 is used to monitor the state of the device, such as the loading state of the filter or the deposition or buildup of material in the element, or the amount, quality or composition of the material in module 136 such as the amount, quality or composition of the fuel, oil, coolant, air, urea, EGR gas, or other material. In one example, probe 128 may be used to detect water, sulfur levels, oxidation state, soot buildup, a change in base number, or some other characteristic of the material within or passing through module 136.

In another example, probe 132 may be mounted in one or more engine cylinders and used to measure the position of the piston within the cylinder, the quality of the combustion process, the emissions produced by the combustion process, the quantity of fuel injected, or any other parameter, such as temperature or pressure. Probe 132 may be mounted in other locations to monitor position within other types of actuators, such as linear or rotational actuators, or void volume in tanks and reservoirs such a liquid tanks for fuel tanks or urea tanks or oil or coolant tanks, in other examples.

In yet another example, probes 126 or 124 may be used to monitor changes in the dielectric properties within module 108. In one embodiment, module 108 is a particulate filter housing containing a particulate filter 114 and a catalyst element 112. Module 108 may contain only a filter or a catalyst, or multiple elements, such as multiple filters and catalysts. The elements within module 108 such as catalyst element 112 or particulate filter 114 may be monitored using probes 126 or 124 in order to determine the state of the filter or catalyst, such as the loading state, aging, poisoning such as by sulfur, ash or soot accumulation or distribution, and the health or integrity of the catalyst element 112 or filter element 114 or module 108. The filter element 114 may or may not also contain a catalyst coating.

In addition, time-resolved measurements of the state of module 108, catalyst element 112 or filter element 114 may be used to determine the rate of material inflow or outflow from the module using probes 126 or 124. In one example, module 108 may be a particulate filter housing and the quantity of accumulated soot on the filter 114 may be determined by radio frequency measurements using probes 126 or 124, such as by monitoring phase, amplitude, frequency or some derivative parameter or combination thereof. In this example, the radio frequency signal may be sampled at a rate faster than 1 sample per second in one embedment, but may be faster or slower. The derivative of the radio frequency signal, or difference in the signal between successive measurements in time, provides an indication of the rate of change of soot accumulation on the filter element 114 in this example. In this manner, the entire filter element 114 may serve as an accumulation soot sensor, to determine the rate of soot accumulation on the filter element 114, not just the total accumulation.

In one example, the combined filter containing module 108 and probes 126 or 124 may function as an engine-out soot sensor, and provide engine feedback control or diagnostic information based on the rate of change of soot accumulation on the filter 114 contained within module 108. Soot oxidation models may or may not be used to compensate for soot oxidation on the filter 114 under certain conditions in this example.

In another example, module 108 may not be a particulate filter housing but may be any type of catalyst, or combined filter and catalysts system, such as a three-way catalyst coated filter, oxidation catalyst coated filter, or selective catalytic reduction coated filter. In a similar manner, the entire catalyst or catalyst coated filter may be used as a gas sensor to determine the inflow rate of a specific gas species, such as NOx, $NH_3$, HC, CO, or some other species based on the monitored rate of change of the RF signal indicative of the adsorption of the specific gas species on the catalyst surface or other interaction of the gas species of interest with the catalyst. The monitored material need not be in the gas phase or particle phase, as in the above examples, but may also be a liquid.

In one example, the monitored radio frequency parameter may be determined from absolute or relative amplitude or phase measurements or some derivative thereof, such as a maximum or minimum value, average value, frequency shift, peak or resonance width at a given power level, quality factor, or a related parameter. The parameter may be determined at a fixed frequency, or over a continuous or discontinuous range of frequencies. The frequencies may or may not include resonant conditions.

The rate of change, (Δ/t), of one or more measured radio frequency parameters, P, may be computed at a specific time, t, as follows:

$$(\Delta/t) = (P_{t-1} - P_t)/((t-1)-t) \qquad \text{Equation 1}$$

where the notation (t−1) indicates a measurement of the parameter P at a previous time and the subscript (t) indicates the current measurement time. In this manner, the module 108 or a portion thereof can be used to determine the rate of a constituent material of interest entering the module. The time may be measured by a timing device included in control unit 104.

Conversely, the same approach can be used to determine the rate of a constituent material of interest escaping from or exiting module 108 or 110 or 136, or conduit 138 or 106. In one example, if the rate of material entering the module 108 is known, under a specific set of conditions, for example, then the rate of change of the material levels within module 108 may be used to detect the escape of loss of material from module 108.

In one example, the loss or leakage of soot or particles from a particulate filter module 108 may be detected in this manner. In this example, operation of the engine at a condition resulting in a known rate of soot output from the engine and a known or negligible quantity of soot oxidation on the particulate filter element 114 may be used as the preferable condition for using the control unit 104 to detect failures of filter element 114 resulting in soot leakage. In this example, the rate of change of soot accumulation on the filter element 114, or the total change in soot accumulation on the filter element 114 over a specified time interval may be compared with the known amount of engine-out soot emissions entering the module 108 during this time period. A difference in the measured soot accumulation on the filter 114 and the quantity of soot entering the filter module 108 may indicate the loss or escape of soot, due to a filter malfunction or failure such as cracked or melted regions if the increase in measured soot levels on the filter 114 is less than the quantity of soot entering module 108. One application of this example is to detect filter failures for on-board diagnostics. The time interval for the measurements may be over several seconds or several minutes in one case, or over an interval of less than one second in another case. The interval may encompass an entire test cycle, such as a drive cycle or modal cycle, or only one particular operating condition. The engine-out soot emissions may be previously determined, or measured by a sensor such as a PM sensor or radio frequency sensor.

In another example, the pre erred time interval for monitoring the change in soot accumulation on the filter or rate of change of soot accumulation on the filter may be during low temperature operation or low-NOx operation, where passive oxidation is limited. In one example, this may be at temperatures below 250 degrees C. In another example, a preferred window for monitoring the change in filter soot levels may be during time periods with low or no oxygen in the exhaust, such as with a gasoline engine for example, regardless of the exhaust temperature. Those skilled in the art will appreciate that many variations in exhaust conditions or aftertreatment system design may exist for which soot oxidation is either negligible or well-characterized (such as by a model) and which may be well-suited or preferential for comparing the rate of soot entering the filter with the monitored rate of accumulation on the filter in order to determine the rate of soot loss from the filter, which may be due to a malfunction such as a crack, melted region, or other defect of the filter or exhaust system.

The above example need not be limited to particulate filters, but any type of filter, membrane, or catalyst system, where a solid, liquid, or gas-phase constituent interacts in a measurable way with module 108, such as by deposition, adsorption, reaction with the interaction walls of 108 or certain elements 112 or 114 contained within 108. In this manner, module 108 may serve as a gas sensor, such as for NOx, CO, HC, $O_2$, $NH_3$, or any other gas, or even a liquid by means of monitoring the change in one or more radio frequency parameters, according to Equation 1. The applications include detecting the inflow or outflow of one or more components from module 108 for control or diagnostic purposes. In this manner, failures of the catalyst, such as by escape of certain gas species (or lack of storage or adsorption of certain gas species), may also be determined, or emissions rate of certain species generated by plant or machine 102 may also be determined for feedback control.

The measurements described above may also be carried o conduit 106, such as by probe 122. Probe 122 may monitor the material passing through or deposited on the walls of conduit 106. In one example, probe 122 in conjunction with control unit 104 may operate as a frequency domain reflectometer or time domain reflectometer to monitor the location of faults, failures, or variations in dielectric properties, blockages, obstructions, or flaws and discontinuities through a portion or all of the components and systems connected to conduit 106. In this manner, multiple elements 112, 114, 118, or 116 may be monitored from a single probe, in one example. In another example, multiple probes may be used. In particular, the variable probing can involve probe 120 mounted on an SCR, LNT, TWC, hydrocarbon trap, ammonia storage catalyst or any other catalyst, and probe 122, mounted upstream or downstream of the module 110.

In another example, conduit 106 may consist of multiple branches or legs with various connections, transitions, cavities, and other elements, such as a conduit network. In one example, the conduit network is a pipeline or distributed pipe system. Probes 122, 120, 124, or 126 may be used to detect faults within the conduit network, such as a broken or disconnected conduit, or a failure of elements within the network such as elements 112, 114, 118, or 116. Failure of an element may result in leakage, such as leakage of retentate from a filter, leakage of gases, liquids, or solids, or some other materials. The failure may be detected by a change in the radio frequency monitored parameter such as an anomalous feature or discontinuity. In another example, failure of an upstream element may result in deposition of material which has escaped from the upstream element on a downstream element or portion of conduit. Detection of the leaked material on the downstream conduit or downstream element may also be used to determine the failure of the upstream element.

Control unit 104 may modify engine combustion or calibration such as fueling, air flow, boost pressure, EGR rates, injection timing, urea or hydrocarbon dosing and related parameters, based on radio frequency measurements of properties and composition of the system inputs. In one application, the blend of petroleum-based fuel and some other fuel, such as ethanol or biodiesel may be monitored. In another example, the quality or composition of urea may be monitored.

Control unit 104 may also alert the operator or trigger a fault condition based on radio frequency measurements of fuel quality, such as high water or sulfur levels. In another example, control unit 104 may alert the operator or trigger a fault condition based on radio frequency measurements of the quality, composition, or level of fuel, oil, coolant, hydraulic fluid, intake air, urea, ammonia-generating components, or other process parameters.

Control unit 104 may further modify engine and exhaust system operation based on exhaust emissions measurements using radio frequency probes mounted in conduit 106 or modules 108 or 110. In one embodiment, module 110 may be an SCR catalyst system and probe 120 may monitor ammonia storage on the SCR catalyst, using reflection measurements, or transmission with a second probe in module 110 (transmission) or using probe 122, mounted upstream or downstream from module 110 or within module 110. Control unit 104 may command urea dosing based on monitored levels of ammonia storage on SCR catalyst element 116. In another embodiment, probe 126 or probe 122 may monitor the SCR catalyst, among other elements within the exhaust system. In another example, radio frequency measurements of ammonia storage on SCR catalyst 116 from probe 120 are used communicate with Engine Control Unit to command engine lean and rich operation such as to produce ammonia from an upstream TWC catalyst, so-called passive SCR.

In another example, module 108 may be a particulate filter system and measurements from probe 126 or 124 may be used to control machine 102 operation such as to induce regeneration by increasing exhaust temperature, hydrocarbon dosing, or any other means, and also to terminate the regeneration or control the rate of temperature rise for the regeneration event.

In one example, element 118 may be an ammonia slip catalyst or small filter element, and measurements from probe 122 may be used to detect ammonia slip or particles passing through an upstream catalyst or filter for diagnostic purposes.

In another example, probe 122, 130 or any other probe may monitor the properties of the material such as any gas, liquid, or solid passing through or contained within conduits 106 or 130 or modules 136, 108, or 110.

In another example, only a single probe, such as probe 126 may be used to transmit a radio frequency signal through the entire exhaust system consisting of conduits 106 and modules 108 and 110 to monitor the processes occurring in each part of the system from a single probe. In this case, a mesh may be used to contain the signal at the exit or outlet section of conduit 106 downstream of module 110. In another example, one or more probes 126 may be used and one or more meshes or screens may be used.

Collectively, the system shown in FIG. 1 forms a radio frequency-based process control system, whereby one or more components or sub-systems may be monitored and controlled by one or more radio-frequency control units 104 in order to optimize operation of plant or machine 102, or any module 108, 110, or 136 or any other component or sub-system shown in FIG. 1. The optimization may include improved efficiency, extended durability, improved performance or output, or any other desired result, as well as the alert to any fault conditions or initiation of protective measures due to a fault condition. The optimization may be achieved by controlling one or more inputs or processes control variables to any component or sub-system shown in FIG. 1. The control may be based on direct feedback control from measurements of each probe, in order to maintain the measured values within a desired range. The control may or may not include supplemental model-based controls or inputs from other sensors or devices.

In addition to controlling system operation as described above, faults or malfunctions or failures may also be detected by control unit 104. Such fault or failure conditions may be detected when a measurement from any of the radio frequency probes shown in FIG. 1 falls outside of an acceptable range, or exceeds or falls below a required threshold value. Faults or failures include excessive emissions, such as particles (soot, ash, or any other particles) or gas such as regulated emissions, or any other material. Other system parameters that may be monitored include parameters required to meet on-board diagnostic requirements.

Potential failure modes or early signs of failure (early warnings or prognostics), as well as catastrophic failures of any subsystems or components shown in FIG. 1 may also be monitored. For example, use of a particulate filter system (module 108) may mask high smoke emissions, such as due to high fuel consumption, high oil consumption, a coolant leak, or related malfunction. Control unit 104 and probe 126 or 124 may be used to detect high smoke, coolant, or water vapor emissions, which may deposit on filter element 114 or pass through module 108 or conduit 106. Abnormal, such as high levels of ash accumulation on filter element 114 may also be indicative of high oil consumption.

In another example, abnormal emissions (high or low levels) of different gaseous species, such as NOx or ammonia may also be detected based on radio frequency measurements of catalysts in modules 110 or 108. Lubricant and fuel quality and condition may also be monitored by probe 130 or 128 to diagnose poor quality fuel or abnormal lubricant aging, or the presence of high soot levels or wear metal levels for example. Poor combustion may also directly be detected by probe 132. The loading state of catalyst elements 112, 114, 116, as well as catalyst aging, poisoning, or other characteristics of performance degradation or changes over time may also be monitored.

Control unit 104 may also utilize inputs from other sensors such as temperature sensors, pressure sensors, gas composition sensors, position sensors, and the like, which are not radio frequency based, but are not shown in FIG. 1.

In another embodiment, elements 136, 112, 114, 118, or 116 may be utilized as the sensing elements themselves and monitored by microwave means using probes 128, 126, 124, 122, or 120. In one example, filter element 114 is a particulate filter and probe 126 or 124 may rapidly sample the quantity of soot accumulated on the filter element 114. The derivative of the monitored soot load or change in soot load over time, provides a direct measure of engine-out soot emissions. Control unit 104 may provide a feedback control to machine 102 based on the measured engine-out soot emissions from filter element 114. The feedback control may involve modifying combustion parameters in one example. In one example, the sample rate may range from 1 to 10 Hz, but may be faster or slower in some cases. In the same manner, the instantaneous change in the loading state of any element 136, 112, 114, 118, or 116 may be monitored using probes 128, 126, 124, 122, or 120 to provide a real-time or continuous measurement of the rate of material addition, accumulation, adsorption, or loss on any of these materials from the element. In another example, catalyst element 112 is a TWC and the real-time oxygen concentration may be measured by probe 126 or probe 124. In another example, catalyst element 116 is an SCR or LNT and the NOx emissions rate or ammonia dosing rate may be directly monitored. In yet another example, the concentration of a material in a conduit, such as conduit 106 may also be measured.

The system described in reference to FIG. 1 is adapted for use in any application requiring the detection or diagnosis of a filter state. Some examples of specific applications include: internal combustion engines (gasoline, diesel, natural gas, and others) which may utilize an exhaust particulate filter to reduce PM emissions. Specific filters include diesel particulate filters (DPF), gasoline particulate filters (GPF), but many other applications may also be suitable. These types of filters are employed in on-road applications such as passenger cars, trucks, and buses, as well as off-road applications including agriculture and construction equipment, ships, rail/locomotive, stationary and mobile power generation, and many other applications using internal combustion engines. Additional application particularly well-suited include non-conducting filter media, such as ceramic, polymer, or paper filters used for particle filtration from a gas or liquid stream, such as may be found in power plant emission controls, industrial bag houses, mining, pharmaceuticals and chemicals processing and the like.

In one example, the filter may be a ceramic particulate filter, such as a diesel or gasoline particulate filter, which may be installed on a diesel or gasoline engine for any number of on- or off-road applications. The applications may include passenger cars, trucks, buses, construction equipment, agricultural equipment, power generators, ships, locomotives, and the like. In another example, the filter may be any type of suitable filter installed on any suitable application.

The frequency range of operation may be chosen to be any suitable frequency range. In one example, the frequency range may be from 100 MHz to 3,000 MHz. The radio frequency signal may be broad band or narrow band. The signal may or may not include one or more resonant modes in the filter housing. In an example where one or more resonant modes are established in the housing, observed changes in the signal at resonance provide a measure of the change in state of the particulate filter, as well as the spatial location or general region where the change in filter state has occurred. The frequency range of the RF sensor operation may be fixed or variable. In one example, the operating frequency range may be varied based on the filter loading state or condition.

In one method of operation, the radio frequency sensor is used to monitor the accumulation of soot and ash in a particulate filter. Under normal operating conditions, the accumulation of soot or ash affects the radio frequency signal in a predictable manner by reducing the signal amplitude or causing a frequency shift or phase shift in the signal as described in for example U.S. Pat. Nos. 8,384,397; 8,384,396; and 9,144,831. In particular, the changes in frequency, phase, or amplitude, may be most pronounced at resonance. The use of the radio frequency sensors for monitoring the signal changes for one or more resonant modes not only provides information on the spatial (localized) location or changes in loading state on the filter, but monitoring multiple modes covering the entire filer ensures the total or aggregate rate of change in contaminant loading corresponding to the engine-out levels can be accurately measured. The spatial variations or local changes which may be monitored are related to the regions corresponding to high electric fields within the cavity for each resonant mode.

In many cases, however, a malfunction or failure of the system, such as the engine, connected to the particulate filter may result in abnormal exhaust conditions flowing through the filter. Such upstream failures or malfunctions include excessive soot emissions, leakage of water, coolant, oil, or fuel into the system, or any other related failure modes which may introduce foreign material into the exhaust or result in abnormal exhaust emissions levels. Such failures may be the result of an injector failure, turbocharger failure, the use of incorrect or poor quality fuels and lubricants, failures of upstream seals and gaskets, such as valve stem seals, turbocharger seals, cylinder head gaskets, and the like, or even the malfunction of an EGR valve, EGR cooler fouling, or related problem.

Figure 2:
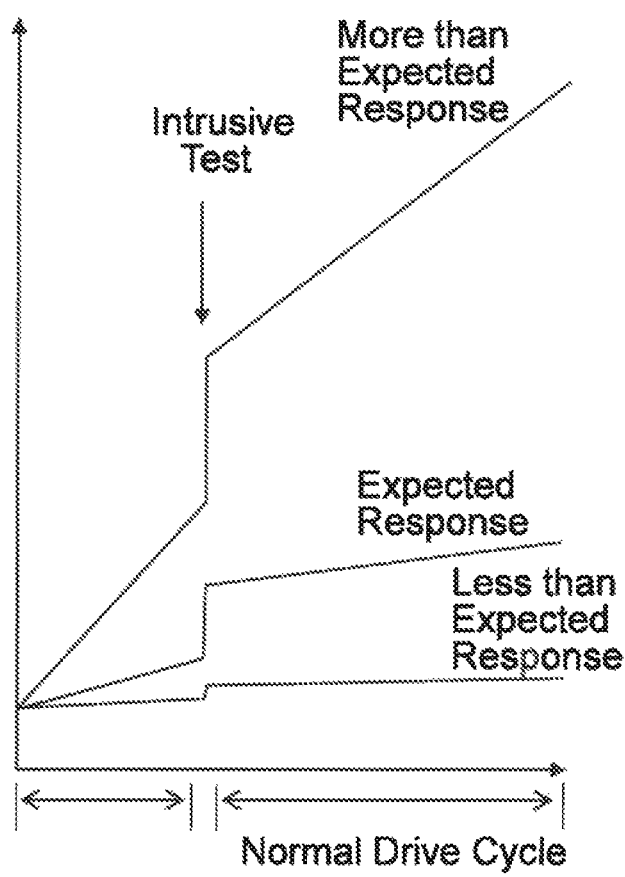
FIGS. 2 and 3 are graphs depicting a comparison of the expected versus actual response for normal drive cycle operation versus intrusive test (stimulus) to probe the system for both actual RF sensor response and (b) rate of change of RF response in accordance with the radio frequency network and system in accordance with the present invention.
Figure 3:
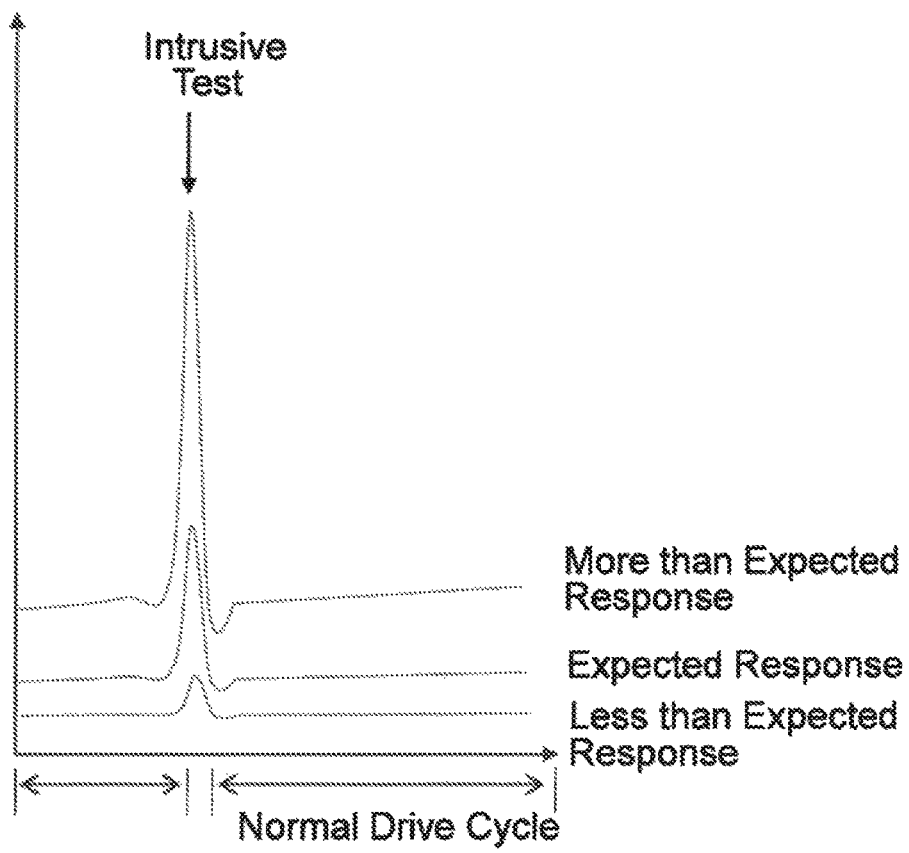

The resulting high-levels of engine-out emissions or contaminants may be detected by abrupt changes (as in the case of catastrophic failure of a component) or slower changes (in the case of progressive component degradation) in the response of the RF sensor. The time rate of change of the sensor response may be monitored to detect instances where the rate of material accumulation on the filter is above a specified threshold value, as shown in FIGS. 2 and 3. The time rate of change in the sensor response may be derived from one or more resonant modes. Monitoring individual modes provides information on the local changes within the filter. Monitoring multiple modes provides information on the total rate of change which may be best correlated to the change in total engine-out soot emissions in one example. In another example, monitoring individual modes may be used to detect local failures in a specific region of the filter. The material accumulation on the filter may be soot, ash, water, coolant, oil, fuel, or some other material (solid, liquid, or gas) which affects the dielectric properties within the filter housing.

The changes in the RF sensor response may be in the signal magnitude, frequency, or phase of the RF signal. An alert or fault indicator may be triggered based on the sensor detecting abnormal filter loading levels. The alert may provide the operator advance warning of a fault condition, before it becomes severe enough to irreversibly damage the filter or further damage the engine or related sub-systems. In another embodiment, the alert or fault condition triggered by the RF sensor may be used to initiate an action and modify the operation of the engine or filter system, such as by de-rating the system, in another example, to avoid damage to the system or filter.

In another method of operation, the RF sensor may be used to detect conditions where soot, ash, or any other material which the filter is designed to trap is escaping from the filter.

In one example, the RF sensor may detect the complete absence of the filter element, such as its removal, by a change in the RF signal (magnitude, frequency, or phase) which is outside a specified or defined range when the filter is present in the system. This range may be defined by the evaluation of current and/or existing operating conditions, and/or a stored or accumulated calculation of the expected baseline of response when a filter is present. In another method of operation, the absence of the filter element is detected as a shift in resonant frequencies or a change in phase or amplitude.

In another embodiment, a partial absence of only a portion of the filter material, such as a cracked, melted, or missing region, may further be detected by changes in the RF signal, such as a shift in resonant frequency in one example, or a change in magnitude or phase in another example. The localized defect may be preferentially detected by only those resonant modes which exhibit a high electric field in the particular region of the filter containing the defect.

In one embodiment, the absence of all or a portion of the filter may result in a shift to higher resonant frequencies for the resonant modes, whereas the loading of material on the filter such as soot or ash may exhibit the opposite behavior, thus allowing defects in the filter material or absence of the filter to be readily detected. In this example, the absence of the filter or defects in the filter may be detected directly by changes in the RF signal without reference to the soot levels or changes in soot levels in the filter.

In another example, the RF sensor may detect abnormally low rates of material accumulation on the filter. The low rate of material accumulation may be detected by comparison of the rate or amount of material accumulated on the filter over a specified period of time with a known rate of material accumulation characteristic of normal filter operation in one example or may be detected by knowledge of upstream emissions rates entering the filter in another example.

The monitoring or determination of low rate of material accumulation may be derived from current and existing RF sensor measurement data, or historical data, but the supplementation of RF sensor measurement data with engine operating information either measured or derived to augment the RF sensor determination of a low rate material accumulation can also be employed. Depending on the distribution of engine or exhaust aftertreatment controllers, additional supplemental information may be provided by other control units in the system.

In one example, if the rate of material accumulation on the filter as measured by the RF sensor is below an acceptable threshold value, the sensor may trigger a fault or alert signal. Filter failure modes which may be detected in this manner include cracks, melted regions, or degradation of the filter matting material, among others, that may result in material escaping from or passing through the filter. The threshold levels may be determined from normal filter operating conditions and drive cycles or engine operating modes. The threshold levels may be based on historical levels when the filter was functioning properly, or pre-set values or limits stored in the sensor or engine or aftertreatment system controller. The engine operation may be adjusted in order to provide a set of conditions with known emission rates, such as particularly high soot concentration in the exhaust, for brief periods of time.

Threshold levels for failure detection may be set for individual resonant modes, such as for the detection of localized failures, or for a parameter derived from more than one resonant mode.

Temperature response of system can also be monitored, mostly to determine that the heat capacity of the system has not changed substantially. The estimated temperature of the unit can be inferred from the temperature compensation, with small changes in loading to the unit, due to fast temperature ramps. With known upstream and downstream temperatures of the exhaust, the filter bed temperature determined from the RF sensor can be used to determine issues in the filter, such as accumulation of large amount of material that do not provide large sensitivity of the signal response, such as oil from an oil leak in the engine, or ash, or exhaust leaks upstream from the filter that result in lower than expected flow rates through the fitter. The problems or failure modes may manifest through changes in the heat capacity of the filter, changes in the flow through the filter, or others. The thermal response can be determined following an active change in the engine operation, or just during normal operating conditions.

The temperature response can also be monitored during an engine off condition, during which the exhaust system including the filter are only subject to ambient environmental influences on the temperature profile as the system cools. The RF sensor can monitor the engine off events, and keep a historical record of how the filter temperature changes based on several measured or derived parameters including, for example, calculated soot load at time of engine shutdown, exhaust temperature at time of engine shutdown, periodic or continuous RF measurement values during the cool down, time for exhaust system to reach a certain temperature, detection of an unintended temperature rise after engine shutdown, etc. The timing in which this kind of monitoring takes place can vary depending on conditions, but would be enabled by the engine no longer being in a combustion mode.

In another example, engine on events may also be monitored in a similar manner. The measured filter state determined at engine off may also be compared with the measured filter state determined at engine on to detect changes In the filter state or faults. Similarly, the filter state may be monitored periodically even with the engine off. The parameters monitored during engine on or off events may consist of temperature, RF sensor measurements of filter loading state, such as soot or ash levels, or the raw RF resonance values such as frequency, amplitude, or phase for one or more resonance modes or frequency ranges.

In another embodiment, active means may be employed to evaluate the filters response to a particular external stimulus. In one example, the external stimulus (intrusive test) may be a momentary, controlled increase in engine-out soot emissions, such as by increased fueling, modification to injection timing, control of intake air flow (throttling), change in exhaust gas recirculation (EGR), or manipulation of boost pressure, among others. The expected changes in soot generation by the engine will have an expected signature as dictated by the coordination of the intrusive request by the RF sensor to the control units who govern the engine and control parameters that can control the generation of soot. This soot signature may be a temporary increase in soot emissions, a temporary decrease in soot emissions, or an intelligent signature such as pulses or dithering as examples.

The resulting changes in engine-out soot emissions may be monitored by the RF sensor. The changes in engine-out soot emissions is expected to result in a change in the filter loading level that can be correlated to the expected emissions from the engine based on the RF signal response. The monitoring or determination of the expected soot level response as requested intrusively, may be derived from current and existing RF sensor measurement data, but the supplementation of RF sensor measurement data with engine operating information either measured or derived to augment the RF sensor determination of the response can also be employed. Depending on the distribution of engine or exhaust aftertreatment controllers, additional supplemental information may be provided by other control units in the system.

The intrusive testing may be conducted periodically or continuously. In one embodiment, the preferable condition for conducting a radio frequency measurement is an intrusive test conducted or determined when conditions are preferable, such as conditions for negligible soot oxidation on the filter in one example, or conditions where soot oxidation is well-known in another example. Other considerations may be used to determine preferable conditions for conducting the intrusive test, aside from soot oxidation.

The detection of a fault condition, such as loading levels above or below threshold value may be conducted over normal operating conditions or drive cycles, shown in FIGS. 2 and 3.

FIG. 2 shows the measured RF response while FIG. 3 shows the derivative response (change with respect to time). In one example, a more or less than expected RF response over normal engine operation or drive cycle may be used to determine whether a system fault or malfunction has occurred, such has high engine-out soot, oil, coolant levels, or any other contaminant entering the filter, or whether a filter failure or malfunction has occurred causing a loss of material from the filter or reduced trapping efficiency of the filter such as a cracked, melted, or missing region.

FIG. 3 shows additional differences in the expected response of the RF signal to failure modes related to the derivative response of the RF sensor (time rate of change).

FIGS. 2 and 3 also illustrate the detection of faults, failures, or malfunctions through the use of an intrusive test which may be triggered at one or more times during the course of normal engine or vehicle operation. The intrusive test may be used to detect system failures or malfunctions, diagnose the condition of the system, or to confirm or validate the results of measurements conducted during normal engine or vehicle operation.

In another embodiment, the RF response to certain system inputs such as throttle, engine speed or fueling may be determined in order to relate the input to the output RF signal via a transfer function. Using simple feedback loops, the expected RF signal response may be compared to the actual response providing an error signal which may be used to diagnose filter failures or abnormal engine operation without requiring any specific input shaping to the system.

In another embodiment, the RF sensor is monitoring the filter regeneration event for oxidizing the accumulated soot in the filter. Based on the calculated or measured soot storage amount in the filter, the RF sensor can store information about previous filter regenerations events including, for example, peak regeneration temperature (sensed directly by the RF sensor or provide externally from other control units), rate of soot oxidation, soot loading level achieved after a complete regeneration, soot loading level achieved after a partial regeneration, time duration of the regeneration event, and/or similar performance information.

Evaluating the differences in regeneration events compared to historical events provides an evaluation mechanism to determine if the fitters response is indicative of a structural failure. The monitoring or determination of the expected soot level may be derived from current and existing RF sensor measurement data, but the supplementation of RF sensor measurement data with engine operating information either measured or derived to augment the RF sensor determination of the response can also be employed. Depending on the distribution of engine or exhaust aftertreatment controllers, additional supplemental information may be provided by other control units in the system.

In another example, the rate of soot oxidation may be used to deduce the health or state of the catalyst or the upstream engine-out conditions. In one embodiment a slower than expected soot oxidation rate as measured by the RF sensor may be used to diagnose aging or loss of catalyst activity of the catalyzed particulate filter or upstream oxidation catalyst.

In another example, the reduced soot oxidation rate may be due to a reduction in engine-out NOx emissions or higher than expected PM-to-NOx ratio. The regeneration process and soot oxidation rate monitored by the RF sensor may be an active regeneration or a passive regeneration or a combination of active and passive regeneration.

In another example, the catalyst health or activity of the catalyzed filter or upstream oxidation catalyst may be determined by a combination of exhaust temperature measurements and RF sensor measurements of the soot oxidation rate at a given temperature or the change in soot oxidation rate at a given temperature.

If the rate of change of response of the RF signal, or the relative change in the RF signal response, is lower or higher than expected from the external stimulus, then a filter failure condition may exist whereby soot or other material is passing through the filter. The specific stimulus applied to the system may be predefined, to establish a well-known and "normal" response with an intact filter. The stimulus may occur periodically or continuously. The frequency of the application of the active stimulus may also be fixed or variable, depending on the circumstances. Examples of variations from the expected response are shown in FIGS. 2 and 3.

The active stimulus need not result in excessive or high levels of material addition to the filter, but may also be designed to induce loss of material from the fitter, should a filter failure condition exist. In one example, commanding high exhaust flow rates, such as by rapidly increasing the engine speed, may result in a spike or pulse of exhaust gas flow. Such a pulse in the exhaust flow may result in material being blown off the filter or through the filter, should the filter contain a defect or flaw (cracked, melted, or failed region). The decrease in the monitored filter loading level determined by the RF sensor, following the application of such an active stimulus is directly indicative of a filter failure condition.

The application of the active stimulus can be used in conjunction with the RF sensor to detect filter failure conditions. In one example, the active stimulus may only be used to avoid false positive indications of fitter failures (confirm the presence of a failure), such as following an initial indication of lower than expected material accumulation on the filter over the course of normal engine operation, as shown in FIG. 3. In this case, if below normal material accumulation levels (slow rate of material accumulation) are detected by the RF sensor, then the sensor or engine control unit may request the application of an active stimulus to further probe or test the system to confirm the existence of a filter failure. Sequential application of active stimuli of increasing magnitude may be applied to further probe or confirm the existence of a filter failure condition.

Determination of whether or not filter loading levels or the rate of material accumulation on the filter, as measured by the RF sensor, is within or outside of acceptable bounds may be accomplished through one or several means.

In one example, the level or rate of material accumulation may be compared with historical values over similar operating conditions, or it may be compared with fixed values or threshold levels such as those stored in a computer readable storage medium on the microcontroller in the form of a look-up table.

In another example, the RF sensor response may be compared with the results of predictive models used to estimate engine-out emissions levels under certain conditions in another example.

In another example, the RF sensor response to loading levels on the filter may be compared with measurements of upstream sensors. In yet another example machine learning techniques may be employed such as neural networks in one example, and pattern recognition in another example, to detect anomalous changes in the RF signal.

The RF measurements may require some type of compensation, such as temperature compensation. In one embodiment, the monitoring of the filter health using RF means may be continuous. In another embodiment, the RF sensor may only monitor the filter health during periods of system operation when it is more favorable to do so, such as low exhaust temperature conditions, in one example, or high temperature conditions in another example. Monitoring the filter at high temperature conditions or low temperature conditions may provide some advantages for materials exhibiting temperature-dependent dielectric properties. In yet another example, a preferred time period for monitoring filter health may be in a clean filter state in one example, and in another example a preferred favorable period for monitoring filter health may be in a loaded state.

The change from the expected signal to the measured one can be used to determine issues or failure with either the filter itself, the engine, or the instrument. Re-calibration of the unit and self-diagnostics can be used to determine failures with the measuring unit or its components (cables, antennas, power supplies, communication).

The RF signal may be modified such as by modifying the frequency range and/or modifying the amplitude of the signal. In one example, the frequency range of interest may be modified to specifically probe a certain region of the filter, such as by exciting a particular resonant mode in one example. In another example, the RF output signal amplitude may be modified, such as by means of an adjustable gain or other mechanism. In yet another example, the RF output amplitude may be adjusted to meet a specified amplitude at the receive port (which may or may not be one in the same as the transmit port) and the applied gain may serve as an indicator of the filter state, as opposed to the detected magnitude. In another example, the phase of the signal may be varied, such as by introducing a phase shift in the signal.

The detection of a filter failure condition tray be used to trigger an alarm, alert the operator, trigger a fault condition, or initiate an action. Examples include the illumination of an indicator lamp, or the modification of engine operation. In another example, detection of a filter failure condition may be used to trigger further diagnostic measurements or actions, such as an intrusive test in one example, to confirm or more narrowly pin-point the failure or malfunction.

Figure 4:
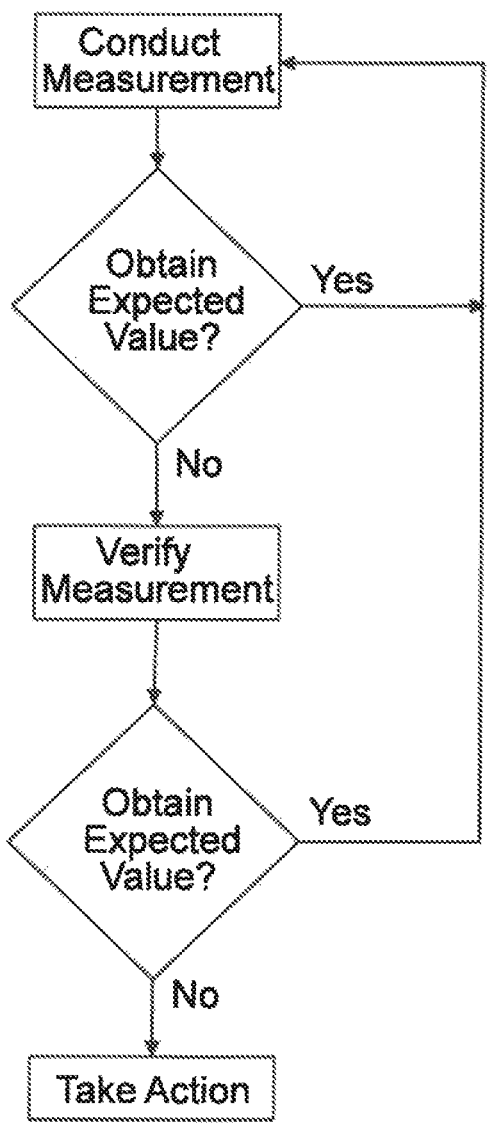
FIG. 4 is a process flow diagram or methodology in accordance with the network or system of the present invention for determining abnormal filter conditions and validating the detection of a fault condition before initiating an action in which the sequence may be perform any order and the verification step may be performed once or several times.

FIG. 4 provides one example showing a flow chart and decision steps for diagnosing the state of the system. In a first step an RF measurement is conducted. The measurement output may be a calibrated value such as the soot or ash level in the filter, in one example, or an intermediate value such as the raw RF magnitude, frequency, or phase measurements, or a parameter derived therefrom, or the resonance curve corresponding to one or more resonant modes. The measurement may include RF measurements or measurements from other sensors, or data such as historical data, model output or calculated data, or values stored in a control unit, such as in a lookup table in one example.

In a second comparison step, the measurement is compared with an expected value to determine whether or not the measurement is within an acceptable range or above or below a threshold value. The comparison may be made with the calibrated RF sensor output, or the raw RF resonance data, or some derivative thereof. In another example the comparison step may determine whether the RF resonance signal characteristics, such as peaks, notches, or other characteristics or parameters derived therefrom are consistent with expected behavior or are anomalous.

The outcome of the comparison step may be to repeat the measurement or verify the measurement. In one example if no fault or malfunction is detected, the measurement loop may simply be repeated. In another example if the comparison or decision step detects anomalous, unexpected, or abnormal behavior of the RF signal or combination of RF measurements and other sensor measurements or computed, derived, or predicted parameters, or the measurement value is out of range or above or below an acceptable threshold, the measurement may be verified in a subsequent step.

Any number of methods or steps may be used to verify the measurement. The measurement may be repeated in one example to determine if the same value or conclusion is reached. In another example a different measurement may be conducted, such as an intrusive test shown in FIGS. 2 and 3 in order to provide a different measurement of the system to determine whether or not the same conclusion is reached in a subsequent decision step. The verification and subsequent comparison or decision step may be repeated any number of times to definitively confirm the presence or absence of a fault condition, or to more accurately pin-point or specify the type, location, or severity of the fault or malfunction or detect related faults or malfunctions.

In one example, a general fault indicating a reduction in filter trapping efficiency (material escaping from the filter) may be used to determine that a filter failure exists, based on a parameter computed from the aggregate resonance curves. In this example a subsequent verification step may involve scanning a different frequency range or different resonant modes, or more precisely scanning specific resonant modes with higher frequency resolution to more accurately pin-point the location or severity of the failure. In another example intrusive tests may be used to alter the inputs to the system to confirm or verify the fault. In yet another example, plausibility or rationality checks may be conducted such as by comparing values from one or more sensors, or from one or more models or reference values to confirm the correct operation of the sensors conducting the measurements which serve as inputs to the decision steps used to detect a fault or diagnose the system. The verification step may be conducted once, more than once, or not at all.

In a last step, an action may be initiated based on the results of a previous comparison step. If the previous comparison step detects a system fault or malfunction an action may be initiated which may consist of alerting the operator such as by an alarm or turning on a lamp or indicator, or initiating a protective action such as by modifying the system operation in another example. In yet another example the action may log or transmit a fault code. In another example the action may shut of the engine, plant or machine. In another action the engine or plant may be de-rated. Any number of actions may be initiated.

Numerous variations and modifications of the embodiments of the radio frequency process sensing, control, and diagnostics network and system and methods and examples of sensing, control, and diagnostics described above may be effected without departing from the spirit and scope of the novel features of the invention. It is to be understood that no limitations with respect to the radio frequency process sensing, control, and diagnostics network and system and methods and examples of sensing, control, and diagnostics and, more specifically, the radio frequency particulate filter diagnostics system and methods and examples of sensing, control, and diagnostics described herein are intended or should be inferred. It is, of course, intended to cover by the appended claims all such modifications as fall within the scope of the claims.

What is claimed is:

1. A radio frequency sensing, control, and particulate matter diagnostics system comprising:
   a housing including an inlet connected to a source of particulate matter;
   a particulate filter in the housing adapted for filtering the particulate matter;
   a radio frequency sensor adapted to detect conditions of abnormal particulate filter or system operation, the radio frequency sensor including at least one radio frequency probe in contact with the housing for the particulate filter and adapted to receive radio frequency signals;

and a radio frequency control unit in communication with the radio frequency probe, the source of particulate matter being an engine and the radio frequency sensor is adapted to monitor engine shutdown events and the radio frequency control unit stores a historical record of changes in the temperature response of the system based on selected measured or derived parameters, the measured or derived parameters including calculated particulate matter load at the time of engine shutdown, exhaust temperature at the time of engine shutdown, periodic or continuous radio frequency measurement values during cool down of the engine, time for the system to reach a threshold temperature, and detection of an unintended rise in temperature after engine shutdown.

2. The system of claim 1, wherein the radio frequency sensor is adapted to monitor the time rate of change of the response of the radio frequency sensor to detect a rate of particulate matter accumulation in the particulate filter above or below a threshold value.

3. The system of claim 1, wherein the particulate matter is soot, ash, water, coolant, oil, or fuel.

4. The system of claim 1, wherein the radio frequency sensor monitors the time rate of change in the magnitude, frequency or phase of the radio frequency signals.

5. The system of claim 1, wherein the radio frequency sensor is adapted to detect a rate of accumulation of particulate matter below a threshold rate via a comparison of the rate of particulate matter accumulated in the particulate filter over a defined period of time with a known rate of particulate matter accumulation during normal filter operation.

6. The system of claim 1, wherein the radio frequency sensor is adapted to sense the response of the system to selected system inputs in order to relate the input and output radio frequency signals via a transfer function.

7. The system of claim 1, wherein the source of particulate matter is an engine, the particulate matter is soot, and the radio frequency sensor is adapted to monitor a particulate filter regeneration event for oxidizing the accumulated soot in the particulate filter.

8. The system of claim 1, wherein the radio frequency sensor is adapted to monitor the response of the system to an external stimulus.

9. The system of claim 8, wherein the external stimulus is a momentary, controlled increase or decrease in particulate matter emissions.

10. The system of claim 8, wherein the radio frequency sensor is adapted to monitor changes in an expected particulate matter signature in response to the external stimulus and the expected particulate matter signature is derived from existing radio frequency sensor measurement data.

* * * * *